(12) United States Patent
Lyons et al.

(10) Patent No.: US 7,307,071 B2
(45) Date of Patent: Dec. 11, 2007

(54) RAF-MEK-ERK PATHWAY INHIBITORS TO TREAT CANCER

(75) Inventors: John F. Lyons, Moraga, CA (US); Gideon Bollag, Hercules, CA (US)

(73) Assignee: Onyx Pharmaceuticals, Inc, Emeryville, CA (US)

( * ) Notice: Subject to any disclaimer, the term of this patent is extended or adjusted under 35 U.S.C. 154(b) by 490 days.

(21) Appl. No.: 10/308,721

(22) Filed: Dec. 3, 2002

(65) Prior Publication Data
US 2003/0125359 A1 Jul. 3, 2003

Related U.S. Application Data

(60) Provisional application No. 60/336,886, filed on Dec. 4, 2001.

(51) Int. Cl.
| | |
|---|---|
| *A61K 31/025* | (2006.01) |
| *A61K 31/03* | (2006.01) |
| *A61K 31/13* | (2006.01) |
| *A61K 31/075* | (2006.01) |
| *A61K 31/08* | (2006.01) |
| *A61K 31/17* | (2006.01) |
| *A61K 31/33* | (2006.01) |

(52) U.S. Cl. ............. 514/183; 514/588; 514/591; 514/596; 514/597; 514/619; 514/620; 514/647; 514/660; 514/670; 514/672; 514/673; 514/716; 514/717; 514/718; 514/719; 514/721; 514/722; 514/747; 514/749; 514/751

(58) Field of Classification Search .......... None
See application file for complete search history.

(56) References Cited

U.S. PATENT DOCUMENTS

| 4,414,928 A * | 11/1983 | Nakada ............. 123/73 PP |
| 5,040,496 A | 8/1991 | Plohberger et al. |
| 7,025,021 B1 * | 4/2006 | Andersson et al. ...... 123/73 PP |
| 7,100,550 B2 * | 9/2006 | Sheldon et al. .......... 123/65 P |

FOREIGN PATENT DOCUMENTS

| WO | WO 94/26260 | * 11/1994 |
| WO | WO 97/36587 | * 10/1997 |
| WO | WO03/013540 | * 2/2003 |

OTHER PUBLICATIONS

Messenger et al (Molecular and Cellular Biology, 1997, vol. 17, pp. 3229-3241).*

* cited by examiner

*Primary Examiner*—Karen A. Canella
(74) *Attorney, Agent, or Firm*—Gregory Giotta

(57) ABSTRACT

Materials and methods for treating certain cancers are described, preferably cancers that result from the up-regulation of the RAF-MEK-ERK pathway, and more preferably chronic myelogenous leukemia, and which cancer is preferably resistant to the inhibition of the Bcr-Abl tyrosine kinase, imatinib.

8 Claims, 5 Drawing Sheets

BAY 43-9006

Anti-Proliferation Effect of BAY43-9006 on Imatinib$^R$ Cell Lines (48 hr.)

Effect of Bay 43-9006 and Imatinib on Phospho-ERK Levels of Bcr-Abl Transformed Cell Lines.

RAF-MEK-ERK PATHWAY INHIBITORS TO TREAT CANCER

This application claims priority from U.S. Provisional Patent Application No. 60/336,886, filed Dec. 4, 2001

FIELD OF THE INVENTION

The invention described herein is in the field of cancer therapy, and preferably for the treatment of chronic myelogenous leukemia.

BACKGROUND OF THE INVENTION

A goal of modern cancer therapy is to identify molecules in signal transduction pathways that affect cell growth, and particularly those that cause a normal cell to become cancerous. One such pathway is the RAF-MEK-ERK pathway, and the up-regulation of one or more of its members is thought to be responsible for a number of cancers. For example, patients with chronic myelogenous leukemia, herein after referred to as CML, who are in either the chronic or blast phase typical achieve remissions in response to the marketed drug Gleevec™, also referred to as imatinib or STI571 (*N. Eng. J. Med.* 244, 1031 [2001]; *N. Eng. J. Med* 244, 1038 [2001]). CML is characterized by the Philadelphia chromosomal translocation (Ph+) resulting in a Bcr-Abl fusion protein. Imatinib treats CML by blocking Bcr-Abl kinase activity.

While the remissions achieved with imatinib during the chronic phase of CML are durable, patients with remissions achieved during the blast phase usually relapse within 2-6 months (*N. Eng. J. Med.* 244, 1038 [2001]). Resistance to Imatinib results in reactivation of Bcr-Abl kinase activity. Recently, it has been shown that these relapses are usually due to imatinib-resistance that occur either by over-expression of the translocated Bcr/Abl gene, or mutation of the imatinib target gene, namely the Abl kinase (*Science* 293, 876 [2001]). Resistance often correlates with mutations in the Abl kinase domain, including T315I and E255K.

The Abl kinase was chosen as a molecular target in the treatment against cancer since 95% of patients with CML have activation of the Abl pathway that occurs through chromosomal translocations that result in fusion of the Bcr and Abl genes. As mentioned above, a key pathway that is up-regulated in CML cells that are resistant to imatinib is the RAF-MEK-ERK pathway. Therefore, treatment with inhibitors of the RAF-MEK-ERK pathway should lead to remissions in patients with imatinib resistant CML.

SUMMARY OF THE INVENTION

The invention described herein presents methods and compositions for treating cancers that involve up-regulation of one or more molecules in the pathway: RAF-MEK-ERK.

An object of the invention is a description of inhibitors of the RAF-MEK-ERK pathway that are beneficially applied to the treatment of certain forms of cancer, preferably CML, and more preferably to those forms of CML that are resistant to Bcr-Abl kinase inhibitors, and most preferably to those forms of CML that are resistant to the Bcr-Abl kinase inhibitor, imatinib.

Another object of the invention is a description of RAF inhibitors, preferably Bay 43-9006, alone or in combination with Bcr-Abl kinase inhibitors, preferably imatinib, for the treatment of CML.

Still another object of the invention is a description of MEK inhibitors, preferably CI-1040, alone or in combination with Bcr-Abl kinase inhibitors, preferably imatinib, for the treatment of CML.

Another object of the invention is a description of methods and compositions for formulating and administering inhibitors of the RAF-MEK-ERK pathway, preferably in combination with Bcr-Abl kinase inhibitors and more preferably with the Bcr-Abl kinase inhibitor, imatinib.

These and other objects of the present invention will become apparent to a skilled practitioner of the art upon a full consideration of the invention.

DESCRIPTION OF THE INVENTION

All publications, including patents and patent applications, mentioned in this specification are herein incorporated by reference to the same extent as if each individual publication was specifically and individually indicated to be incorporated by reference in its entirety.

Figure 1:
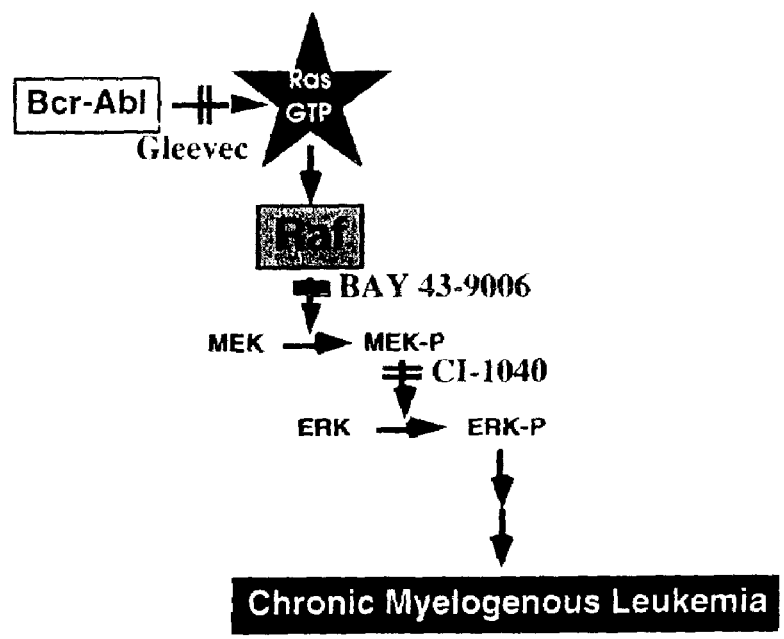
FIG. 1 shows the RAF-MEK-ERK pathway that becomes up-regulated in certain cancer cells, including chronic myelogenous leukemia. Also shown are the compounds BAY 43-9006, and CI-1040, and the proteins in the pathway that they affect, RAF and MEK, respectively.
Figure 2:
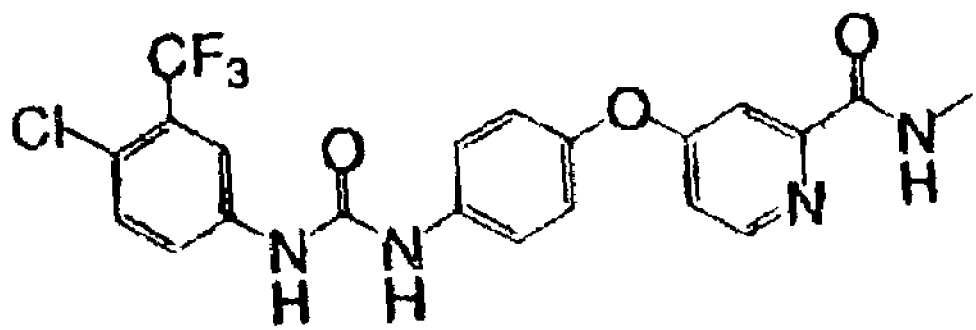
FIG. 2 shows the structure of BAY 43-9006.

Based on the pathway shown in FIG. 1, it will be appreciated that in cancers where Raf, MEK, or ERK are up-regulated, compounds that inhibit the activities of these molecules will have beneficial effects for treating such cancers. An example of one such cancer, also shown in FIG. 1, is chronic myelogenous leukemia. Thus, treating patients with non-toxic doses of, preferably, 200-400 mg and higher of the Raf kinase inhibitor BAY 43-9006 (*Endocr. Relat. Cancer* 8, 219 [2001]) will result in remissions, or minimally stabilization of the growth of the cancer. Furthermore, treating patients with non-toxic doses of, preferably, 200-400 mg and higher of the MEK inhibitor PD184352 (now designated CI-1040, *Oncogene* 19, 6594 (2000) will also lead to remissions or cancer growth stabilization in these patients.

Definitions

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art.

BAY 43-9006 is described in U.S. patent application Ser. No. 09/425,228 and PCT/US00/00648, as are numerous other RAF kinase inhibitors.

The MEK inhibitor, CI-1040, is described in *Oncogene* 19, 6594 (2000).

Imatinib, or Gleevec,™ is described in U.S. Pat. No. 5,521,184.

By "up-regulated" or "up-regulation" of the RAF-MEK-ERK pathway is meant elevated levels, by whatever molecular mechanism, of one or more of the proteins, RAF MEK, or ERK, or increases in their enzymatic activity, or changes in their normal substrate affinity when compared to normal cells.

It will be appreciated that the compounds that affect RAF, MEK, or ERK may be used alone, or in combination. They may also be used in combination with other compounds known to affect particular cancers where the RAF-MEK-ERK pathway is up-regulated. For example, the drug imatinib (Gleevec™) is used to treat CML patients; thus, imatinib resistance that develops in certain advanced staged CML patients that causes up-regulation of the RAF-MEK-ERK pathway can be treated with the appropriate compounds that control the up-regulation of the appropriate molecules in the RAF-MEK-ERK pathway. Such compounds can be combined with imatinib for treatment of a CML patient before imatinib resistance develops, or without imatinib after resistance has developed. The pathway in question and the sites of action of BAY 43-9006, CI-1040 and imatinib are illustrated in FIG. 1.

There are several important rationale for applying inhibitors to the RAF-MEK-ERK pathway for the treatment of CML. First, cells from leukemia patients (Ph+) have elevated phospho-ERK levels at least in part due to elevated, or up-regulated, RAF kinase activity. Second, imatinib treatment results in decreased phospho-ERK levels. Also, cells from imatinib-resistant patients have re-elevated phospho-ERK levels.

Pharmaceutical Compositions and Modes of Administration

The present invention also relates to pharmaceutical compositions for administration to humans that comprise an inhibitor of the RAF-MEK-ERK pathway alone, or in combination with imatinib. Such would include compositions for enteral administration, such as nasal, buccal, rectal or, especially, oral, and parenteral administration, such as intravenous, intramuscular or subcutaneous. The compositions comprise the inhibitor on its own or, preferably, together with a pharmaceutically acceptable carrier. The dose of inhibitor depends on the disease to be treated, preferably CML, and more preferably imatinib resistant CML, and the age, weight and individual condition of a patient, and the mode of administration.

The invention relates also to processes, and to the use of inhibitors of the RAF-MEK-ERK pathway in the preparation of pharmaceutical compositions alone, or in combination with imatinib. Preference is given to a pharmaceutical composition that is suitable for administration to a human suffering from a cancer that is responsive to inhibition of a protein tyrosine kinase. Preferably the cancer is CML, and more preferably it is imatinib resistant CML which composition comprises an inhibitor, or a salt thereof where salt-forming groups are present, in an amount that is effective in inhibiting the protein tyrosine kinase, together with at least one pharmaceutically acceptable carrier.

Preference is also given to a pharmaceutical composition for the prophylactic or, especially, therapeutic treatment of preferably CML, and more preferably imatinib-resistant CML, which composition comprises as active ingredient an inhibitor, or a pharmaceutically acceptable salt thereof, in an amount that is prophylactically or, especially, therapeutically effective against the mentioned diseases.

The pharmaceutical compositions comprise from approximately 1% to approximately 95% of the appropriate inhibitor, dosage forms that are in single dose form preferably comprising from approximately 20% to approximately 90% active ingredient, and dosage forms that are not in single dose form preferably comprising from approximately 5% to approximately 20% active ingredient. Unit dose forms are, for example, dragees, tablets, ampoules, vials, suppositories or capsules. Other dosage forms are, for example, ointments, creams, pastes, foams, drops, sprays, dispersions, etc. The pharmaceutical compositions of the present invention are prepared in a manner known per se, for example by means of conventional mixing, granulating, confectioning, dissolving or lyophilising processes.

There are preferably solutions that can be used with the appropriate inhibitor, including suspensions or dispersions, especially isotonic aqueous solutions, dispersions or suspensions, which, for example in the case of lyophilized compositions comprising the active ingredient on its own or together with a carrier, e.g. mannitol, may be prepared before use. The pharmaceutical compositions may be sterilized and/or may comprise excipients, for example preservatives, stabilizers, wetting agents and/or emulsifiers, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxy-methylcellulose, carboxymethylcellulose, dextran, polyvinylpyrrolidone or gelatin, or also solubilisers, for example .RTM.Tween 80>polyoxyethylene(20) sorbitan monooleate; trademark of ICI Americas, Inc, USA.

Synthetic or semi-synthetic oils as are know in the art may used for injection of the appropriate inhibitor. Particularly useful can be liquid fatty acid esters which contain a long-chain fatty acid having from 8 to 22, especially from 12 to 22, carbon atoms.

Pharmaceutical compositions will preferably be used in oral form, and can be obtained, for example, by combining a RAF-MEK-ERK pathway inhibitor, with or without a Bcr-Abl tyrosine kinase inhibitor, with one or more solid carriers, granulating a resulting mixture, where appropriate, and processing the mixture or granules, if desired, where appropriate with the addition of additional excipients, to form tablets or dragee cores. Suitable carriers are especially fillers, such as sugars, for example lactose, saccharose, mannitol or sorbitol, cellulose preparations and/or calcium phosphates, for example tri-calcium phosphate or calcium hydrogen phosphate, and also binders, such as starches, for example corn, wheat, flee or potato starch, methylcellulose, hydroxypropylmethyl-cellulose, sodium carboxymethylcellulose and/or polyvinylpyrrolidone, and/or, if desired, disintegrators, such as the above-mentioned starches and also carboxymethyl starch, cross-linked polyvinylpyrrolidone, or alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Pharmaceutical compositions for oral administration are also hard gelatin capsules, and soft sealed capsules consisting of gelatin and a plasticiser, such as glycerol or sorbitol. The hard gelatin capsules may comprise an appropriate inhibitor in the form of granules, for example in admixture with fillers, such as corn starch, binders and/or glidants, such as talc or magnesium stearate, and, where appropriate, stabilizers. In soft capsules the active ingredient is preferably dissolved or suspended in suitable liquid excipients, such as fatty oils, paraffin oil or liquid polyethylene glycols or fatty acid esters of ethylene glycol or propylene glycol, it likewise being possible to add stabilizers and detergents, for example of the polyoxyethylene sorbitan fatty acid ester type.

Other oral dosage forms are, for example, syrups prepared in customary manner which comprise the appropriate inhibitor, for example, in suspended form and in a concentration of approximately from 5% to 20%, preferably approximately 10% or in a similar concentration that provides a suitable single dose when administered, for example, in a measure of 5 or 10 ml. Also suitable are, for example, powdered or liquid concentrates for the preparation of shakes, for example in milk. Such concentrates may also be packed in single dose quantities.

For parenteral administration of the appropriate inhibitor there are suitable, especially, aqueous solutions of an active ingredient in water-soluble form, for example in the form of a water-soluble salt, or aqueous injection suspensions that comprise viscosity-increasing substances, for example sodium carboxymethylcellulose, sorbitol and/or dextran, and, if desired, stabilizers. The active ingredient, where appropriate together with excipients, can also be in the form of a lyophilisate and be made into a solution prior to parenteral administration by the addition of suitable solvents.

The instant invention relates to a method for the treatment of the pathological conditions mentioned above, especially those which are responsive to inhibition of tyrosine protein kinases, preferably CML, and more preferably CML that is resistant to Bcr-Abl tyrosine kinase inhibitors. Thus a RAF-MEK-ERK pathway inhibitor, with or without a Bcr-Abl tyrosine kinase inhibitor, may be administered prophylactically or therapeutically as such, or in the form of a pharmaceutical composition.

The Examples which follow are illustrative of specific embodiments of the invention, and various uses thereof. They are set forth for explanatory purposes only, and are not to be taken as limiting the invention

EXAMPLES

Example 1

Effect of RAF Kinase Inhibitor on Imatinib-Resistant CML Cells

To test whether CML cells, and in particular imatinib-resistant CML cells, are sensitive to inhibition of the RAF-MEK-ERK pathway, we analyzed the response of these cells to the Raf inhibitor BAY 43-9006, and to imatinib. Parental IL3-dependent Ba/F3 mouse hematopoietic cells, and derivative cell lines (obtained from Dr. Charles Sawyers, University of California at Los Angeles, and described by Tipping A. J., et al., in Leukemia, 2002, Dec; 16(12):2349-57) that are independent of IL3 due to exogenous expression of wild type Bcr-Abl, or two of the most frequently reported Bcr-Abl kinase domain mutants, E255K and T315I, were exposed to either imatinib or BAY 43-9006. The Bcr-Abl kinase domain mutants E255K and T315I are resistant to imatinib.

Briefly, cell culture methods were as follows. Ba/F3 mouse pre-B cells containing empty expression vector (Ba/F3) or stable expressing wildtype Bcr-Abl (P210 WT), or the imatinib resistant T315I or E255K mutants (P210 T315I, P210 E255K) were cultured in RPMI medium containing 10% serum. Cell proliferation assays were performed as follows. On day 1, $2\times10^5$ cells were plated in 24 well plates with 1.2 ml of media. The appropriate compound, at the chosen concentration was then added to the media in a final DMSO concentration of 0.2%. On day 3, the cells were resuspended, and 0.5 ml of the cell suspension was and diluted with PBS (1:2). Finally, cell proliferation (cell viability) was measured by trypan blue dye exclusion using CEDEX system (Innovatis).

Figure 3:
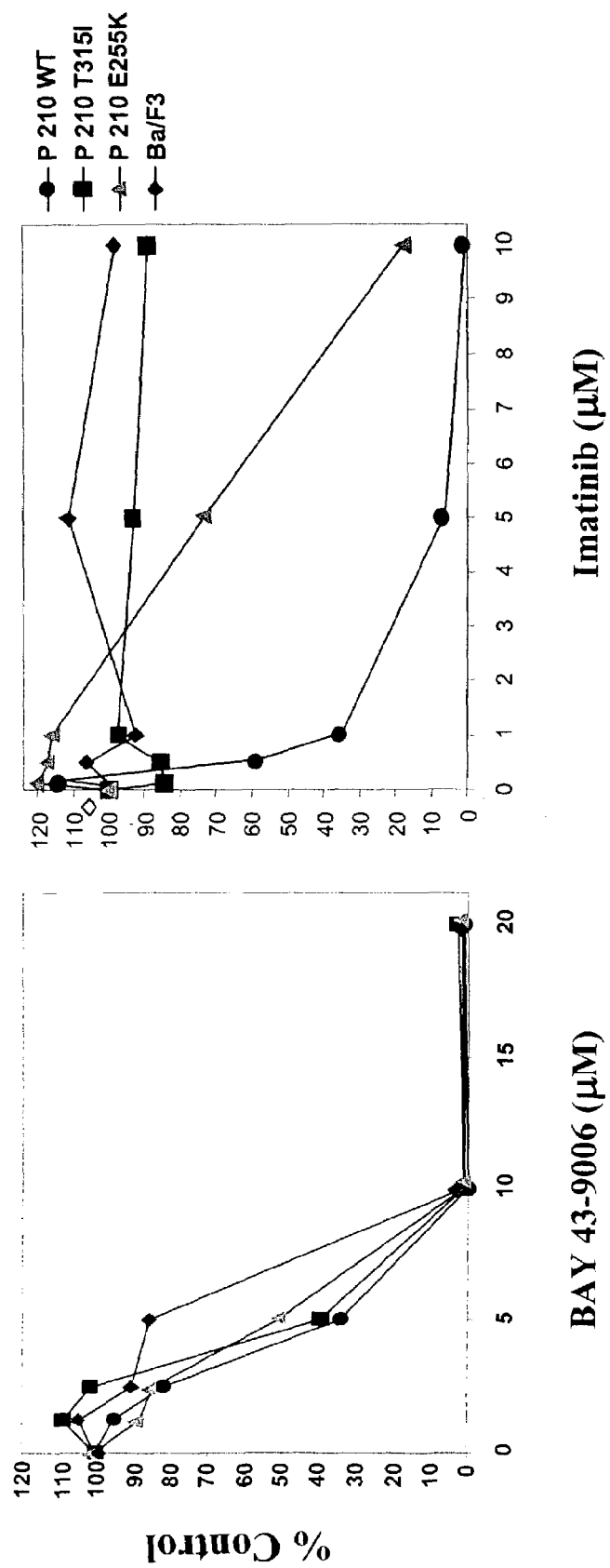
FIG. 3 shows the effects of the RAF kinase inhibitor, BAY 43-9006, and imatinib, on imatinib-resistant CML Cells.
Figure 4:
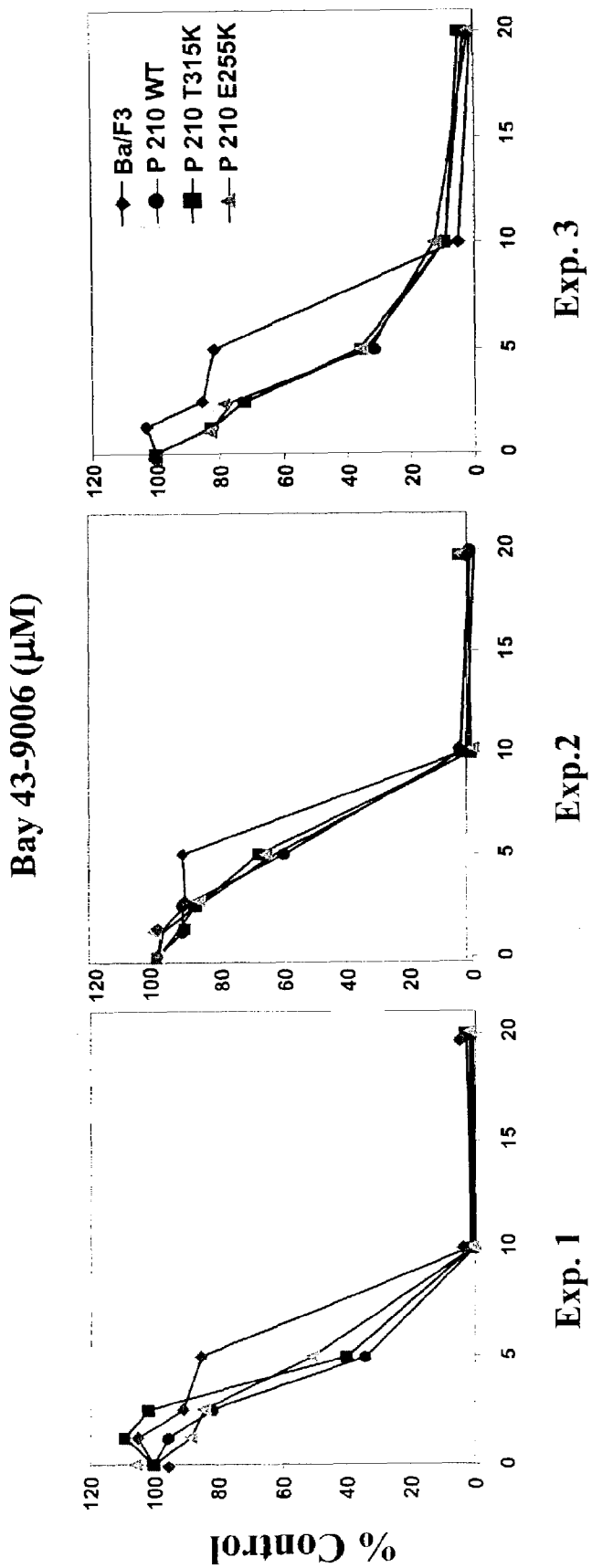
FIG. 4 shows the effects of the RAF kinase inhibitor, BAY 43-9006, on imatinib-resistant CML Cells. The results are from 3 experiments.

The results are shown in FIG. 3. Only those Ba/F3 cells expressing wild type Bcr-Abl were sensitive to imatinib. IC50s for inhibition by imatinib were 0.5 µM for the wild type expressing cells and over ten-fold higher for the three other cell lines. In contrast, as shown in FIG. 4, the proliferation of all four cell lines was inhibited by BAY 43-9006, with IC50s ranging from 4-8 µM.

Thus, these results suggest that CML patients who are or are not resistant to imatinib would respond favorably to inhibitors of the RAF-MEK-ERK pathway such as the Raf inhibitor, BAY 43-9006.

Example 2

Effect of Raf Inhibitor on ERK Phosphorylation

A second experiment was conducted to further establish that sensitivity to imatinib and BAY 43-9006 correlates with inhibition of the RAF-MEK-ERK pathway, as determined by measurement of Erk phosphorylation. The experiment was conducted using parental IL3-dependent Ba/F3 mouse hematopoietic cells, and derivative cell lines that are independent of IL3 due to exogenous expression of wildtype Bcr-Abl, or two of the most frequently reported Bcr-Abl kinase imatinib resistant domain mutants E255K and T315I (obtained from Dr. Charles Sawyers, University of California at Los Angeles, and described by Shah, N., et al. (August 2002) Cancer Cell, vol. 2: pages 117-125). The experiment was conducted as follows. On day 1, $2\times10^6$ cells were plated in a 6 well plate in medium containing 10% serum, and on day 2 the cells were treated with the relevant compound dissolved in DMSO. The final DMSO concentration was 0.2%. Next, the cells were spun down, and washed once with 2 ml of ice-cold phosphate buffered saline, and then lysed with 150 ml buffer. Next, 50 ul of cell lysates was electrophoresed in 10% Tris-Glycine gels, followed by treatment with a 1° antibody which was a phospho-ERK polyclonal rabbit antibody used at 1:1000 dilution. It was obtained from Cell Signaling. The 1° was followed by a 2° antibody which was goat anti-rabbit horse radish peroxidase antibody, and it was used at a dilution of 1:1000. Lastly, Westerns were developed with an ECL kit obtained from Amersham.

Figure 5:
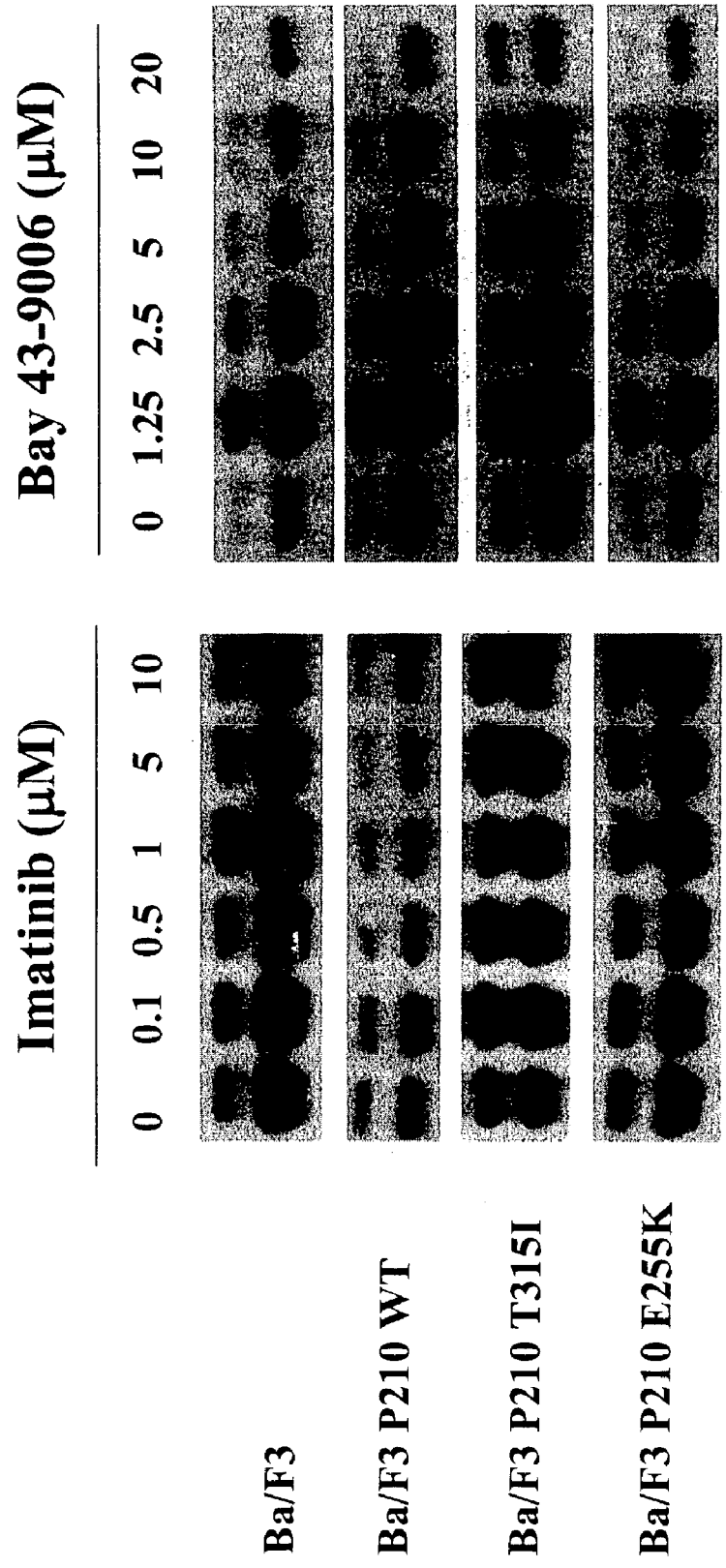
FIG. 5 shows the effects of the RAF kinase inhibitor, BAY 43-9006, on ERK phosphorylation.

FIG. 5 shows the results. Only those Ba/F3 cells expressing wild type Bcr-Abl were sensitive to imatinib. In contrast, phospho-ERK levels in these cells, as well as Bcr-Abl kinase imatinib resistant domain mutants, E255K and T315I, also showed a decrease in phospho-ERK levels in the presence of BAY 43-9006.

These results suggest that CML patients who are or are not resistant to imatinib would respond to inhibitors of the RAF-MEK-ERK pathway such as the RAF inhibitor, BAY 43-9006.

The invention now being fully described, it will be apparent to one of ordinary skill in the art that many changes and modifications can be made thereto without departing from the spirit or scope of the appended claims.

We claim:

1. A method for treating a patient suffering from cancer, wherein said patients' cancer exhibits up-regulation of the RAF-MEK-ERK pathway, comprising administering to the cancer patient an effective dose of an inhibitor of said RAF-MEK-ERK pathway, wherein said cancer is CML, and said inhibitor is selected from the group consisting of Bay 43-9006 and CI-1040.

2. The method of claim 1, wherein said CML is resistant to an inhibitor of Bcr-Abl tyrosine kinase.

3. The method of claim 2, wherein said inhibitor of Bcr-Abl tyrosine kinase is imatinib.

4. The method of claim 2, wherein said inhibitor of the RAF-MEF-ERK pathway is Bay 43-9006.

5. The method of claim 2, wherein said inhibitor of the RAF-MEF-ERK pathway is CI-1040.

6. The method of claim 1, further comprising administering an inhibitor of Bcr-Abl tyrosine kinase.

7. The method of claim 6, wherein said inhibitor of the RAF-MEF-ERK pathway is Bay 43-9006.

8. The method of claim 6, wherein said inhibitor of the RAF-MEF-ERK pathway is CI-1040.

* * * * *